United States Patent
Hashimoto

(10) Patent No.: US 9,770,229 B2
(45) Date of Patent: Sep. 26, 2017

(54) MEDICAL INTERVENTION INSTRUMENT

(75) Inventor: Tatsutoshi Hashimoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 2522 days.

(21) Appl. No.: 12/028,430

(22) Filed: Feb. 8, 2008

(65) Prior Publication Data

US 2008/0195144 A1    Aug. 14, 2008

Related U.S. Application Data

(63) Continuation of application No. PCT/JP2006/315829, filed on Aug. 10, 2006.

(30) Foreign Application Priority Data

Aug. 11, 2005    (JP) ................................. P2005-233004

(51) Int. Cl.
*A61B 17/00*    (2006.01)
*A61B 10/06*    (2006.01)
(Continued)

(52) U.S. Cl.
CPC ............... *A61B 10/06* (2013.01); *A61B 17/29* (2013.01); *A61B 90/03* (2016.02);
(Continued)

(58) Field of Classification Search
CPC ......... A61B 10/06; A61B 17/28; A61B 17/29; A61B 2017/2845; A61B 2017/2912;
(Continued)

(56) References Cited

U.S. PATENT DOCUMENTS 4,043,323 A * 8/1977 Komiya ........................ 606/208
5,176,699 A * 1/1993 Markham ..................... 606/208
(Continued)

FOREIGN PATENT DOCUMENTS

EP    2 450 078 A1    6/2006
JP    S51-84290    7/1976
(Continued)

OTHER PUBLICATIONS

Japanese Office Action dated Mar. 15, 2011.
(Continued)

*Primary Examiner* — David Shay
(74) *Attorney, Agent, or Firm* — Scully, Scott, Murphy & Presser, P.C.

(57) ABSTRACT

A grasping forceps 1 includes: a pair of guide sections 7A and 7B that guide maneuvering wires 6A and 6B in a direction of an axial line C of a sheath; an extending-and-retracting member (transmission section) 8 that transmits displacement information of the maneuvering section to the maneuvering wires 6A and 6B and outputs the displacement information to the intervention instrument; a distal direction movement inhibitor section (specific directional movement-inhibitor section) 10 that allows the sheaths of the maneuvering wires 6A and 6B toward the distal end; a proximal direction movement inhibitor section (specific directional movement-inhibitor section) 11 that allows the sheaths of the maneuvering wires 6A and 6B toward the distal end; and an locked-state-releasing section 12 that releases an engaging state of the guide sections 7A and 7B with the distal direction movement inhibitor section 10 or the proximal direction movement inhibitor section 11 based on the displacement input by the maneuvering section. Accordingly, an medical intervention instrument can be provided that can maintain a certain attitude of the intervention instrument (Continued)

once established during intervention even if an external force is applied, and that can carry out identical operations simultaneously, i.e., manipulating of the intervention instrument and releasing of a certain attitude of the intervention instrument.

8 Claims, 13 Drawing Sheets

(51) Int. Cl.
*A61B 17/29* (2006.01)
*A61B 17/28* (2006.01)
*A61B 90/00* (2016.01)

(52) U.S. Cl.
CPC ............... *A61B 2017/2845* (2013.01); *A61B 2017/2911* (2013.01); *A61B 2017/2912* (2013.01); *A61B 2017/2939* (2013.01); *A61B 2017/2946* (2013.01)

(58) Field of Classification Search
CPC .... A61B 2017/2911; A61B 2017/2939; A61B 2017/2946; A61B 90/03
USPC .................................................. 606/205, 208
See application file for complete search history.

(56) References Cited

U.S. PATENT DOCUMENTS

| | | |
|---|---|---|
| 5,766,184 A | 6/1998 | Matsuno et al. |
| 6,440,144 B1 | 8/2002 | Bacher |
| 6,599,295 B1 | 7/2003 | Tornier et al. |
| 2004/0167569 A1 | 8/2004 | Dicesare et al. |
| 2004/0171989 A1 | 9/2004 | Horner et al. |

FOREIGN PATENT DOCUMENTS

| | | |
|---|---|---|
| JP | S51-158193 | 12/1976 |
| JP | 08-126648 | 5/1996 |
| JP | 11-318915 | 11/1999 |
| JP | 2003-126103 | 5/2003 |

OTHER PUBLICATIONS

Extended Supplementary Partial European Search Report dated Mar. 21, 2014, from corresponding European Application No. 06 796 328.0.

* cited by examiner

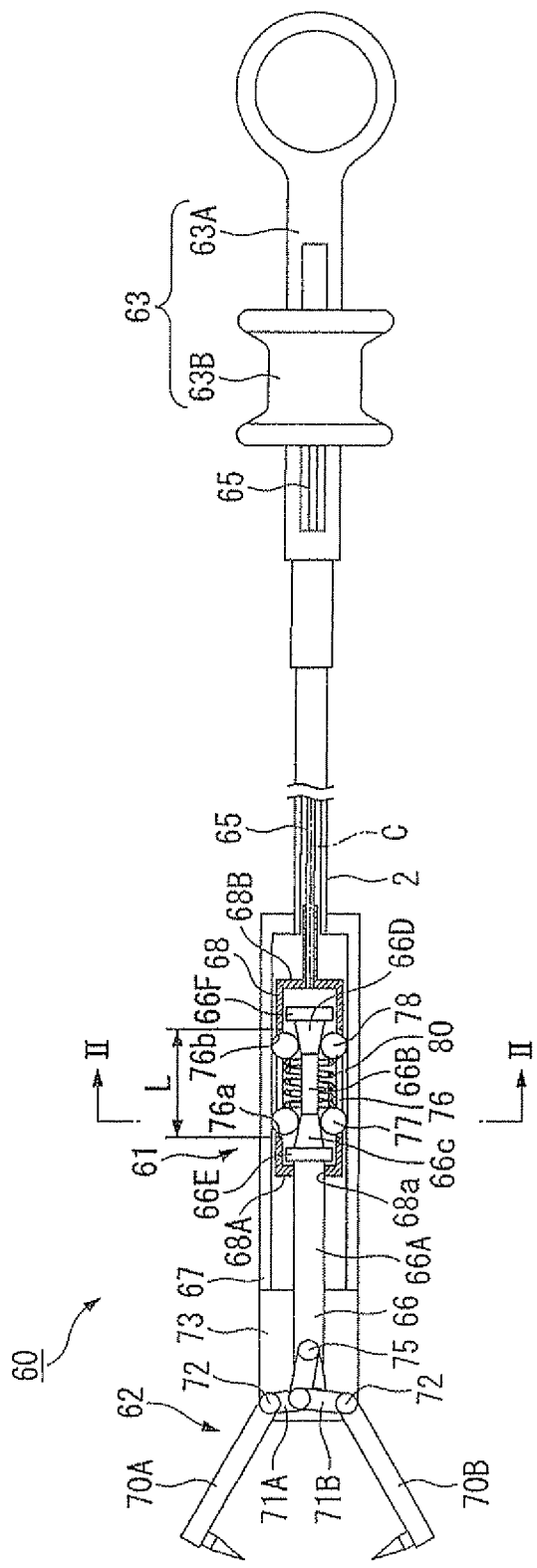
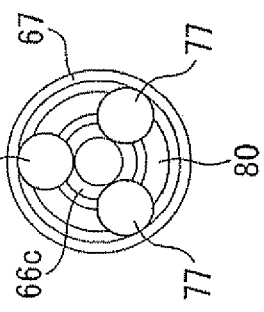
FIG. 11A
FIG. 11B

MEDICAL INTERVENTION INSTRUMENT

The present application is a continuation application based on PCT application No. PCT/JP2006/315829, filed Aug. 10, 2006, in Japan, the content of which is incorporated herein by reference.

BACKGROUND OF THE INVENTION

Field of the Invention

The present invention relates to a medical intervention instrument for use in interventions including surgical or arthroscopic operation.

Description of the Related Art

Various holding mechanisms have been proposed to maintain a certain attitude of an intervention section during an intervention carried out with a medical intervention instrument that manipulates an intervention section connected to the distal end of an elongated sheath with a maneuvering section connected to the proximal end of the sheath. (See, for example, Patent Documents 1 and 2)

The medical intervention instrument disclosed by Patent Document 1 is provided with screws that are adjustable to press a maneuvering wire onto a maneuvering section and limit movement of the maneuvering wire to maintain the attitude of the intervention section. In addition, the maneuvering section of a medical intervention instrument disclosed by Patent Document 2 has a ratchet mechanism that limits movement of a slider toward the distal end by means of a jaw section hooking a groove section formed on the surface of a maneuvering section main unit and maintains the attitude of the intervention section. The slider in this case is movable upon manipulating a ratchet-releasing button disposed on a lateral surface of the maneuvering section.

However, the intervention section disclosed by Patent Document 1 is subject to unintended manner of movement if the medical intervention instrument is applied an external force that is more significant than a friction force between a locking screw and a maneuvering wire fixed by a compressing force by the locking screw. In addition, the jaw section of the medical intervention instrument disclosed by Patent Document 2 cannot be fixed between two groove sections; therefore, the maneuvering wire cannot be held with a predetermined force. Furthermore, separate manipulations associated with the maneuvering section, i.e., actuation of the intervention section and release of the certain attitude of the intervention section immobilize quick transition to next operation.

Patent Document 1: Japanese Unexamined Patent Application, First Publication No. 2003-126103

Patent document 2: Japanese Unexamined Patent Application, First Publication No. H8-126648

SUMMARY OF THE INVENTION

The present invention was conceived in consideration of the aforementioned circumstances, and an object thereof is to provide a medical intervention instrument that can maintain a certain attitude of the intervention section once established during intervention even if an external force is applied, and that can carry out identical operations simultaneously, i.e., manipulating of the intervention section and releasing of a certain attitude of the intervention section.

The present invention adapts following sections for solving the above difficulties.

An medical intervention instrument according to the present invention includes: a sheath having a distal end and a proximal end and extending in an axial direction; an intervention section disposed to the distal end of the sheath; a transmission section that makes extending and retracting movements in an axial line direction relative to the sheath; a maneuvering section, disposed to the proximal end of the sheath, that accepts displacement information input thereinto associated with the transmission section relative to the sheath; a guide section, fixed in the axial line direction relatively against the sheath; a distal direction movement inhibitor section that allows the transmission section to move toward the proximal end of the sheath relative to the guide section; and a proximal direction movement inhibitor section that allows the transmission section to move toward the distal end of the sheath relative to the guide section.

The medical intervention instrument can maintain a certain attitude of the intervention section, necessary to be maintained, that is actuated based on displacement input by the maneuvering section since the distal direction movement inhibitor section can move the transmission section toward the proximal end of the sheath even if an external force directed to the distal end of the sheath is loaded to the transmission section, Also, a certain attitude of the intervention section can be maintained since the proximal direction movement inhibitor section can move the transmission section toward the distal end of the sheath even if an external force directed toward the proximal end of the sheath is loaded.

In addition, in the medical intervention instrument according to Claim 1 of, the distal direction movement inhibitor section is provided with a first fixing section that is displaced relative to the guide section and engages the guide section with the transmission section or detaches the guide section from the transmission section, and a first urging section that urges the first fixing section in a direction that fixes the guide section to the transmission section relatively. Also, the proximal direction movement inhibitor section is provided with a second fixing section that is displaced relative to the guide section in the direction opposite the first fixing section and engages the guide section with the transmission section or detaches the guide section from the transmission section, and a second urging section that urges the second fixing section in a direction that fixes the guide section to the transmission section relatively.

The medical intervention instrument, irrespective to an external force attempting to move the transmission section toward the distal end, can maintain the fixed state of the transmission section with the guide section since the first fixing section is urged by the first urging section. Alternatively, the fixed state of the transmission section with the guide section can be maintained irrespective to the transmission section attempting to move toward the proximal end since the second fixing section is urged by the second urging section. Therefore, a desirable attitude of the intervention section can be maintained even if an external force is applied in either direction.

Also, an medical intervention instrument according to the present invention includes: a sheath having a distal end and a proximal end and extending in an axial direction; an intervention section disposed to the distal end of the sheath; a transmission section that makes extending and retracting movements in an axial line direction relative to the sheath; a maneuvering section, disposed to the proximal end of the sheath, that accepts displacement information input thereinto associated with the transmission section relative to the sheath; a guide section, fixed in the axial line direction relatively against the sheath, that guides the transmission section in the axial line direction of the sheath; a specific directional movement-inhibitor section that allows the transmission section to move toward the proximal end or the proximal end of the sheath relative to the guide section; and a locked-state-releasing section that releases an engaging state between the guide section and the specific directional movement-inhibitor section based on a displacement in another direction that is different from the direction input by the maneuvering section.

The medical intervention instrument moving the locked-state-releasing section either toward the distal end or the proximal end of the sheath can move the transmission section in the corresponding direction by releasing the movement, limited by the specific directional movement-inhibitor section, of the transmission section in the corresponding direction. In addition, identical operations can be carried out simultaneously, i.e., manipulating of the intervention section and releasing of a certain attitude of the intervention section.

In the medical intervention instrument according to Claim 3 of the present invention, the specific directional movement-inhibitor section is provided with: a fixing section that is displaced relative to the guide section and engages the guide section with the transmission section or detaches the guide section from the transmission section; and an urging section that displaces the fixing section in a direction that fixes the guide section to the transmission section relatively. Also the locked-state-releasing section is provided with a fixed-state-releasing section that displaces the fixing section against the urging force of the urging section in a direction that releases the fixed state between the fixing section and the guide section.

The medical intervention instrument, irrespective to an external force attempting to move the transmission section, can maintain the fixed state of the transmission section with the guide section since the urging section maintains the displaced state of the fixing section. Alternatively, moving the fixed-state-releasing section and displacing the fixing section can release the fixed state of the transmission section with the guide section.

Also, in the medical intervention instrument according to the present invention that is the medical intervention instrument according to Claims 3 or 4, the specific directional movement-inhibitor section is disposed to the distal end of the sheath.

The medical intervention instrument can prevent movement of the transmission section in the vicinity of the intervention section more desirably than in a case where movement of the transmission section based on an external force is prevented in the vicinity of the proximal end of the sheath. Therefore, it is possible to prevent erroneous actuation of the intervention section based on an external force applied to an unactuated state of the intervention section more reliably.

The present invention irrespective to an external force applied to the intervention section can maintain a certain attitude, that has been once established in an intervention, of the intervention section unless the maneuvering section is manipulated intentionally. Also, identical operations can be carried out simultaneously, i.e., manipulating of the intervention section and releasing of a certain attitude of the intervention section.

BRIEF DESCRIPTION OF THE DRAWINGS

FIG. 11A is a schematic view of a grasping forceps according to a second embodiment of the present invention.

FIG. 11B is a cross section of the grasping forceps according to the second embodiment of the present invention viewed along II-II line in FIG. 11A.

DESCRIPTION OF THE PREFERRED EMBODIMENTS

Figure 1:
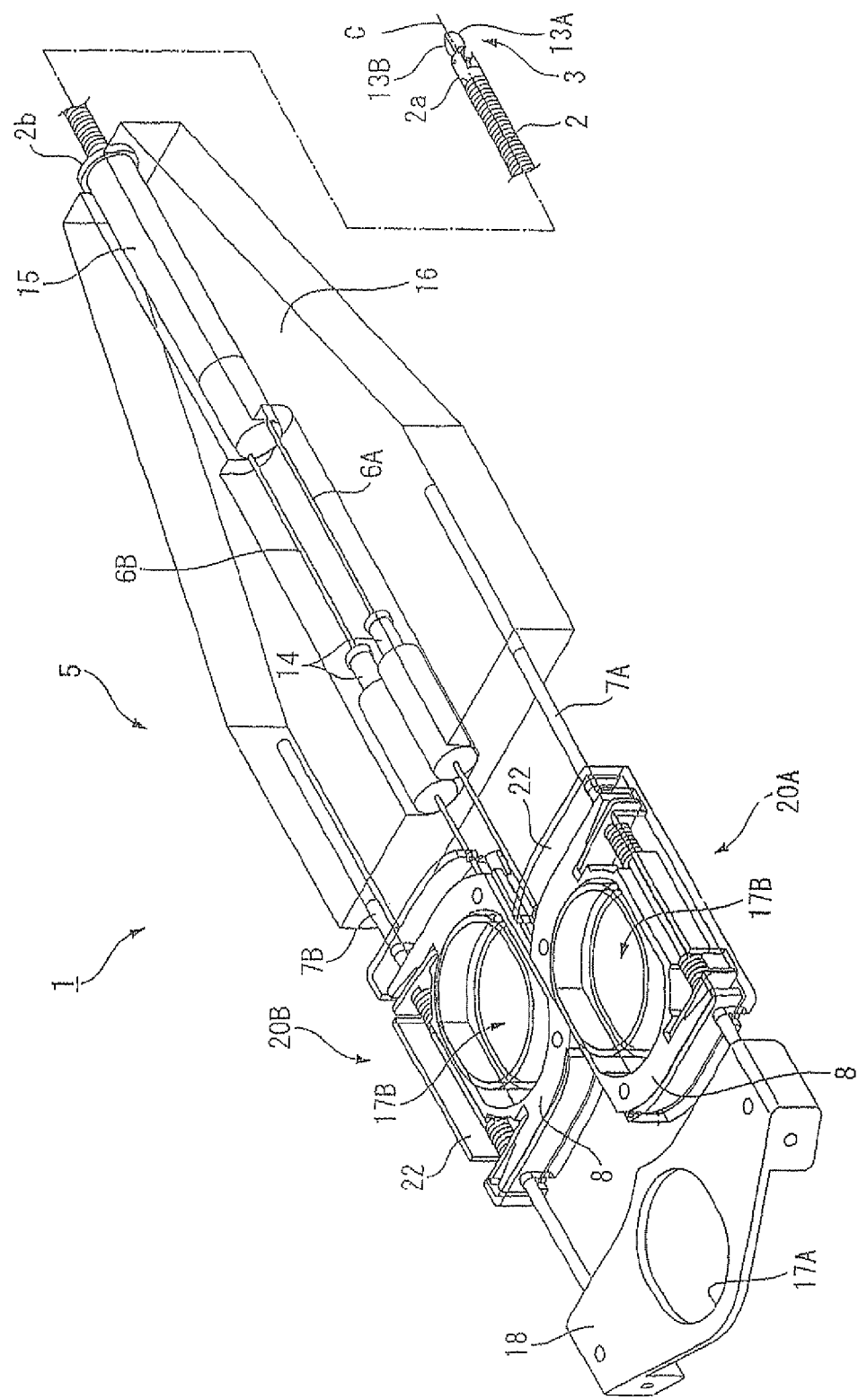
FIG. 1 is a schematic view of a grasping forceps according to a first embodiment of the present invention.
Figure 2:
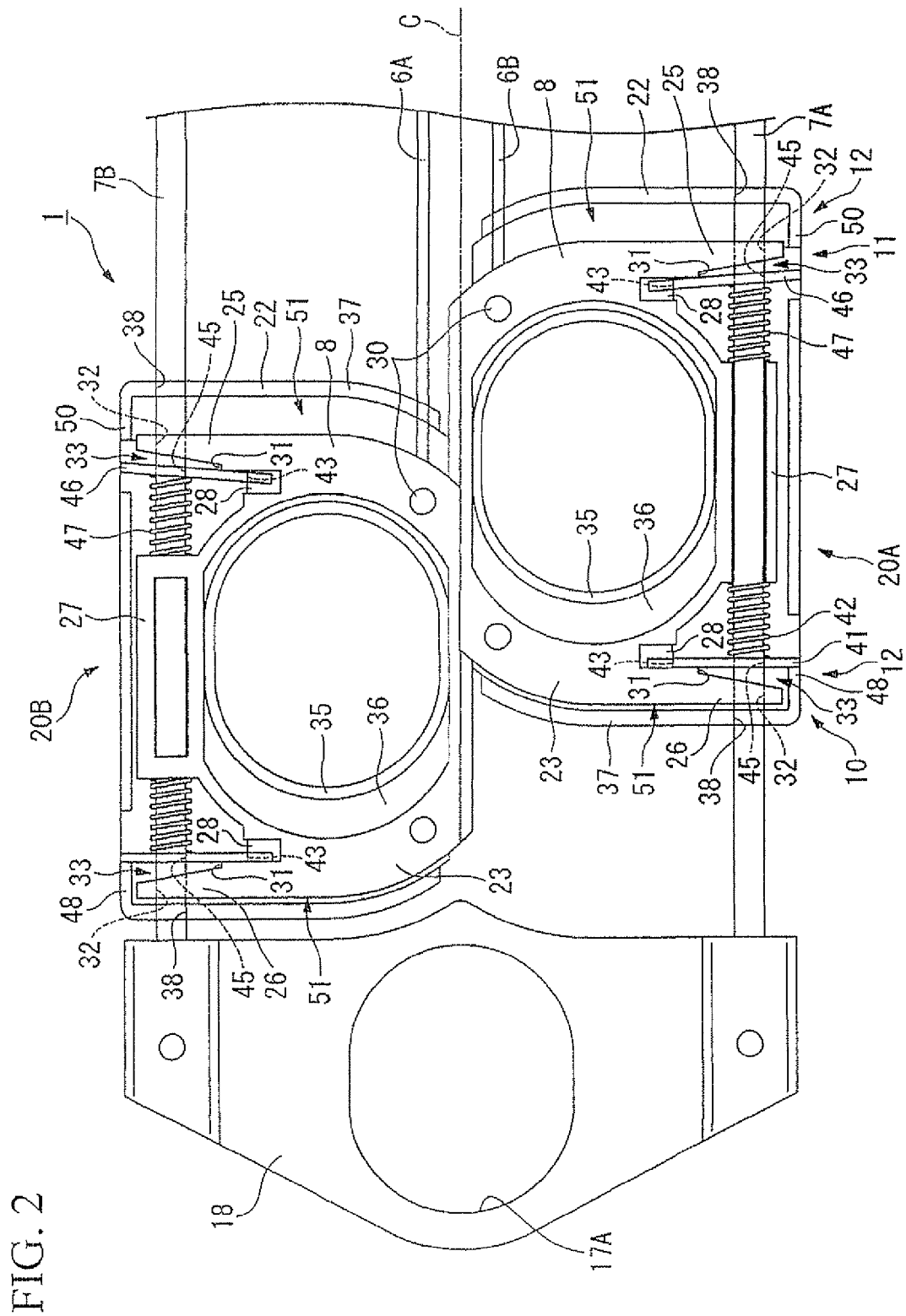
FIG. 2 is a plan view showing a principal part of the grasping forceps according to the first embodiment of the present invention.
Figure 3:
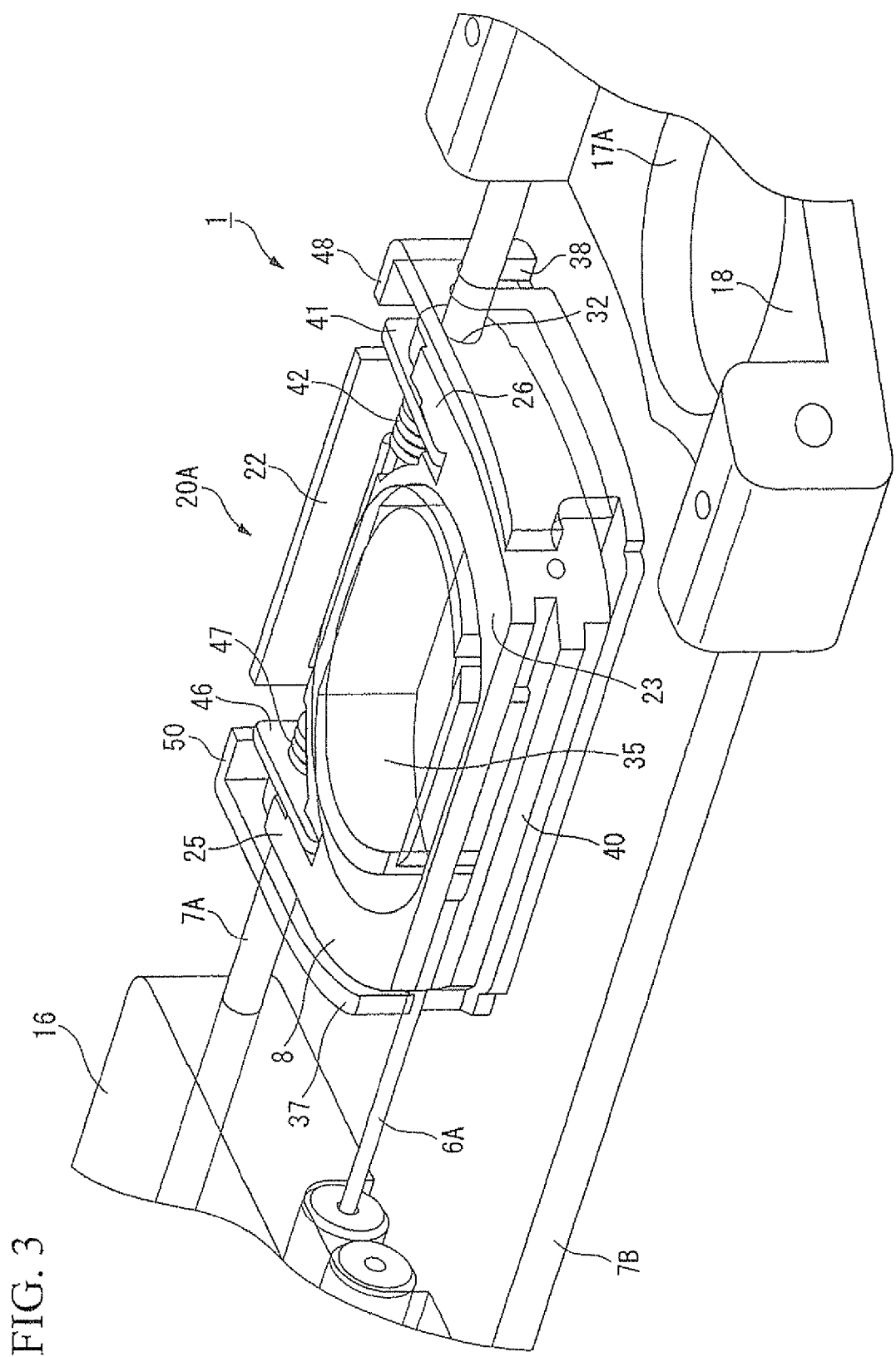
FIG. 3 is a perspective view showing the principal part of the grasping forceps according to the first embodiment of the present invention.

A first embodiment of the present invention will be explained with reference to FIGS. 1 to 10.

As illustrated in FIGS. 1 to 5, a grasping forceps 1 (medical intervention instrument) according to the present embodiment is provided with: a sheath 2 extending in an axial direction and having a distal end 2a and a proximal end 2b; an intervention section 3 disposed at the distal end 2a of the sheath 2; a pair of maneuvering wires 6A and 6B that move in extending and retracting directions along an axial line C of the sheath 2 in the sheath 2; a maneuvering section 5, disposed at the proximal end 2b of the sheath 2, that accepts displacement information associated with the pair of maneuvering wires 6A and 6B relative to the sheath 2; a pair of round bar guide sections 7A and 7B that guide the maneuvering wires 6A and 6B in the axial line C of the sheath 2; a plastic extending-and-retracting member (transmission section) 8, fixed and connected to proximal ends of the maneuvering wires 6A and 6B, that transmits the displacement information of the maneuvering section 5 to the maneuvering wires 6A and 6B and outputs to the intervention section 3; a distal direction movement inhibitor section (specific directional movement-inhibitor section) 10 that allows the maneuvering wires 6A and 6B to move in only the direction toward the proximal end of the sheath 2 relative to the guide sections 7A and 7B; a proximal direction movement inhibitor section (specific directional movement-inhibitor section) 11 that allows the maneuvering wires 6A and 6B to move in only the direction toward the distal end of the sheath 2; and a locked-state-releasing section 12 that releases engagement between the guide sections 7A and 71 and the distal direction movement inhibitor section 10 or the proximal direction movement inhibitor section 11 based on the displacement input from the maneuvering section 5.

The flexible sheath 2 is capable of freely bending.

The intervention section 3 is provided with a pair of grasping jaws 13A and 13B that are connected to the pair of maneuvering wires 6A and 6B via link mechanisms that are not shown in the drawings.

The maneuvering section 5 is provided with: a watertight section 14 that ensures watertightness of the maneuvering wires 6A and 6B; a confluence section 15 of the pair of maneuvering wires 6A and 6B; a watertightness-preserving section 16, fixed and connected to the proximal end 2b of the sheath 2, having the maneuvering wires 6A and 6B and the watertight section 14 in a central area of the watertightness-preserving section 16 along the axial line C of the sheath 2; a fixed handle 18, connected to the other ends of the guide sections 7A and 7B, having a first finger hook section 17A that accepts insertion of a finger; and a pair of slider sections 20A and 20B having a second finger hook section 17B that accepts insertion of another finger in addition to the first finger hook section 17A. The pair of slider sections 20A and 20B move between the watertightness-preserving section 16 and the fixed handle 18 associated respectively with the pair of guide sections 7A and 7B. The pair of guide sections 7A and 7B fixed on both ends of the watertightness-preserving section 16 and having the maneuvering wires 6A and 6B therebetween are disposed in parallel with each other. It should be noted that the pair of maneuvering wires 6A and 6B and the pair of guide sections 7A and 7B are made of a stainless.

Components are in common between the pair of slider sections 20A and 20B except engagement-projection-and-depression sections 40 of a releasing member 22 that will be explained later. The slider section 20A will be explained as follows on behalf of the common components.

The slider section 20A is provided with a transparent plastic releasing member 22 that is capable of extending and retracting relative to the guide section 7A, and relative to the maneuvering wire 6A and the guide section 7A. The slider section 20A contains an extending-and-retracting member 8 that has the maneuvering wire 6A fixed thereto.

It should be noted that both the distal direction movement inhibitor section 10 and the proximal direction movement inhibitor section 11 are disposed to the slider section 20A.

The extending-and-retracting member 8 is provided with: a hoop section 23 that forms the second finger hook section 17B; a distal end projection section 25 and a proximal end projection section 26 that extend in parallel in directions of tangential lines of the hoop section 23 toward the guide section 7A from outer peripheries of the watertightness-preserving section 16 and the fixed handle 18 of the hoop section 23; and a passage section 27 that holds the guide section 7A which extends and retracts in the direction of the axial line C freely so that the passage section 27 is disposed at a tangential line, that is orthogonal to the distal end projection section 25 and the proximal end projection section 26, of the hoop section 23.

A substantial reverse U-shaped saddle section 28 is formed at the section where the hoop section 23 is connected to the distal end projection section 25 and the proximal end projection section 26.

The maneuvering wire 6A is fixed to the extending-and-retracting member 8 via a locking screw 30 at a position that is along the axial line C of the sheath 2.

Respectively provided to the distal end projection section 25 and the proximal end projection section 26 are: cornered sections 31 provided on lateral surfaces that face to each other; and a through-hole 32 that allows the guide section 7A inserted through the passage section 27 to freely extend and retract therethrough relative to the extending-and-retracting member 8.

Each cornered section 31 is formed so that the width of the distal end projection section 25 varies discontiguously in the middle between the distal end and the base of the distal end projection section 25 in the direction of the axial line C. This cornered section 31 is formed so that the shape of the lateral surface of the distal end projection section 25 facing the proximal end projection section 26 makes intimate contact with the front locking plate 46 between the base and the cornered section 31, and a first space 33 having a predetermined width is produced between the cornered section 31 and the distal end, and between the distal end projection section 25 and the front locking plate 46.

A lateral surface of the proximal end projection section 26 facing the distal end projection section 25 also has a cornered section 31.

Provided to the releasing member 22 are: an internal wall section 35, formed along the internal surface of the hoop section 23 of the extending-and-retracting member 8, that forms the second finger hook section 17B by means of the hoop section 23; a bottom section 36, disposed in the exterior of the internal wall section 35, that has the extending-and-retracting member 8 placed thereon; and an external wall section 37 standing from the outer margin of the bottom section 36.

A predetermined backlash formed to the releasing member 22 allows the releasing member 22 to move about in the direction of the axial line C of the sheath 2 relative to the extending-and-retracting member 8 upon placing the extending-and-retracting member 8 on the bottom section 36. In addition, a through-hole 38 is formed to the external wall section 37 so that the guide section 7A that has passed through the passage section 27 of the extending-and-retracting member 8 penetrates through the through-hole 38 extendably and retractably.

Figure 6:
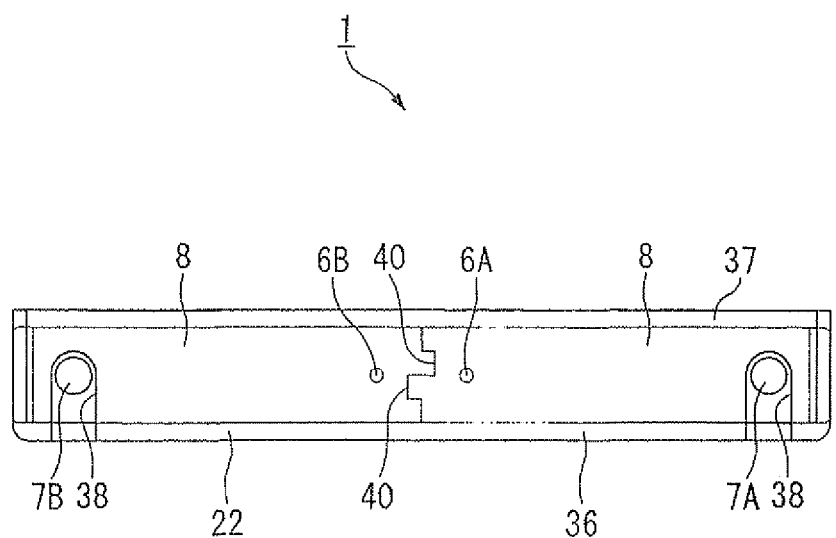
FIG. 6 is a rear view showing the principal part of the grasping forceps according to the first embodiment of the present invention.
Figure 7:
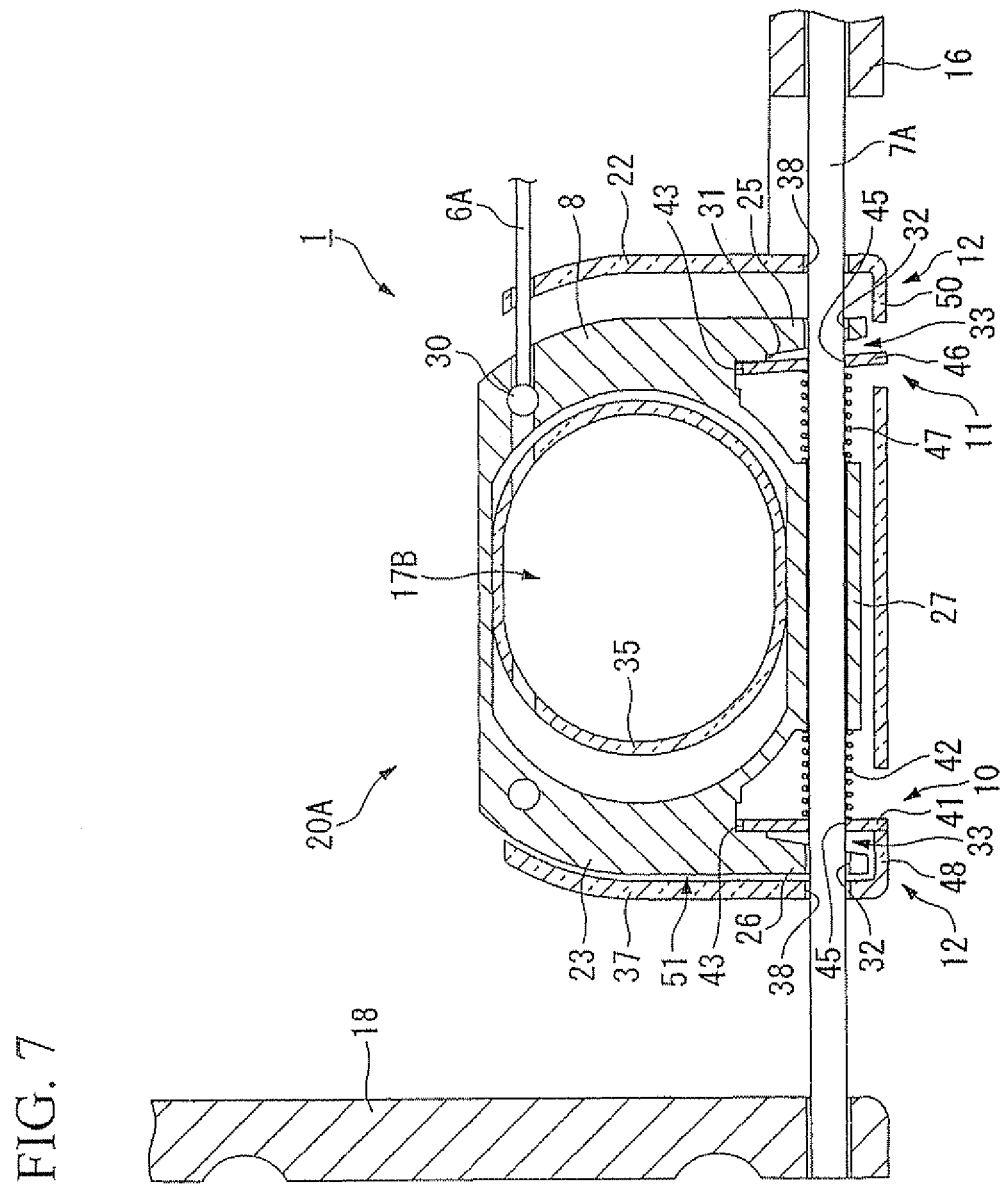
FIG. 7 is a cross sectional view showing how to open the grasping forceps according to the first embodiment of the present invention.
Figure 8:
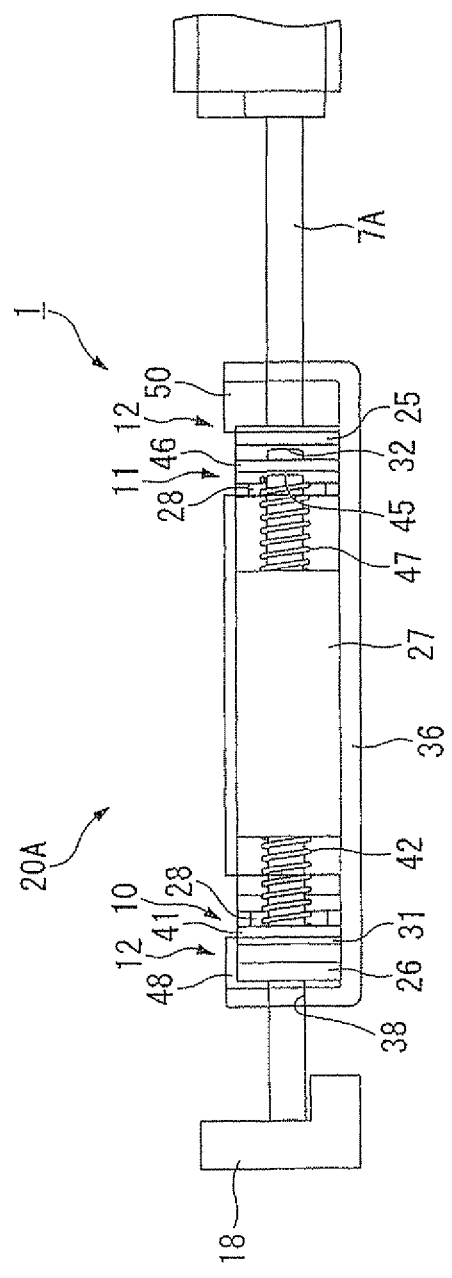
FIG. 8 is a side view of FIG. 7.

An engagement-projection-and-depression section 40 is formed on lateral surfaces of the external wall sections 37 of the slider sections 20A and 20B that face each other as illustrated in FIG. 6. An engaging state of the engagement-projection-and-depression sections 40 is movable relative to the sheath 2. It should be noted that positions of projections and depressions of the engagement-projection-and-depression sections 40 are different between the slider section 20A and the slider section 20B.

The distal direction movement inhibitor section 10 is provided with: a rear locking plate (first fixing section) 41 that engages the guide section 7A to the maneuvering wire 6A or detaches the guide section 7A from the maneuvering wire 6A; and a first urging section 42 that urges the rear locking plate 41 so that the guide section 7A is fixed to the maneuvering wire 6A relatively.

The rectangle-shaped rear locking plate 41 has two ends: an end that has a U-letter-shaped groove 43 which slides in the direction of the axial line C freely while the U-letter-shaped groove 43 engages with the saddle section 28 of the proximal end projection section 26 of the extending-and-retracting member 8; and the other end having a hole section 45 which has an increased diameter that permits a predetermined space to be formed relative to the guide section 7A. As long as the U-letter-shaped groove 43 is engaged to the saddle section 28 and the guide section 7A is inserted through the hole section 45, the rear locking plate 41 is adjusted to displace in a direction in which an angle defined by the rear locking plate 41 and the guide section 7A varies upon sliding the U-letter-shaped groove 43 on the saddle section 28 in the direction of the axial line C.

The rear locking plate 41 is positioned by the first urging section 42 so that the U-letter-shaped groove 43 that is in the vicinity of the sheath 2 relative to the hole section 45 inclines slightly with respect to the direction orthogonal to the guide section 7A, and so that the hole section 45 makes contact with the guide section 7A.

The first urging section 42 is e.g. a helical spring having the guide section 7A inserted therethrough. An end of the first urging section 42 makes contact with the rear locking plate 41, and the other end makes contact with the end section of the passage section 27 of the extending-and-retracting member 8.

The proximal direction movement inhibitor section 11 is provided with: a front locking plate (second fixing section, or fixing section) 46 that can displace in the direction opposite the rear locking plate 41 relative to the guide section 7A and that can engage the guide section 7A to the maneuvering wire 6A and detach the guide section 7A from the maneuvering wire 6A; and a second urging section 47 that urges the front locking plate 46 in the direction that causes the guide section 7A to be fixed to the maneuvering wire 6A relatively.

The front locking plate 46 has the same shape as that of the rear locking plate 41. In addition, the U-letter-shaped groove 43 of the front locking plate 46 engages with the saddle section 28 of the distal end projection section 25 of the extending-and-retracting member 8.

The front locking plate 46 is positioned by the second urging section 47 so that the U-letter-shaped groove 43 that is distant from the sheath 2 relative to the hole section 45 inclines opposite to the rear locking plate 41 slightly with respect to the direction orthogonal to the guide section 7A, and so that the hole section 45 makes contact with the guide section 7A.

The second urging section 47 is also e.g. a helical spring having the guide section 7A inserted therethrough. An end of the second urging section 47 makes contact with the front locking plate 46, and the other end makes contact with the end section of the passage section 27 of the extending-and-retracting member 8.

The locked-state-releasing section 12 is provided with: a rear-locking-plate holder section (fixed-state-releasing section) 48 that presses and displaces the rear locking plate 41 in a direction of releasing the fixed state between the rear locking plate 41 and the guide section 7A against the urging force of the first urging section 42, i.e., in a direction that widens the first space 33; and a front-locking-plate holder section (fixed-state-releasing section) 50 that presses and displaces the front locking plate 46 in a direction of releasing the fixed state between the front locking plate 46 and the guide section 7A against the urging force of the second urging section 47, i.e., in a direction that widens the first space 33.

The rear-locking-plate holder section 48 is disposed to extend by a predetermined length in the direction toward the distal end from the external wall section 37 of the releasing member 22 so that a second space 51 is formed between the extending-and-retracting member 8 and the releasing member 22 when the rear-locking-plate holder section 48 makes contact with the end section of the hole section 45 of the rear locking plate 41.

The front-locking-plate holder section 50 is disposed to extend by a predetermined length in the direction toward the proximal end from the external wall section 37 of the releasing member 22 so that a second space 51 is formed between the extending-and-retracting member 8 and the releasing member 22 when the front-locking-plate holder section 50 makes contact with the end section of the hole section 45 of the front-locking plate 46.

Functions and effects of the grasping forceps 1 according to the present embodiment will be explained next with reference to FIGS. 7 to 10.

Activity of maintaining static state of the slider sections 20A and 20B will be explained first upon undergoing an external force that opens or closes the pair of grasping jaws 13A and 13B. It should be noted that only the slider section 20A will be explained as follows on behalf of common activity carried out by the slider sections 20A and 20B.

Figure 4:
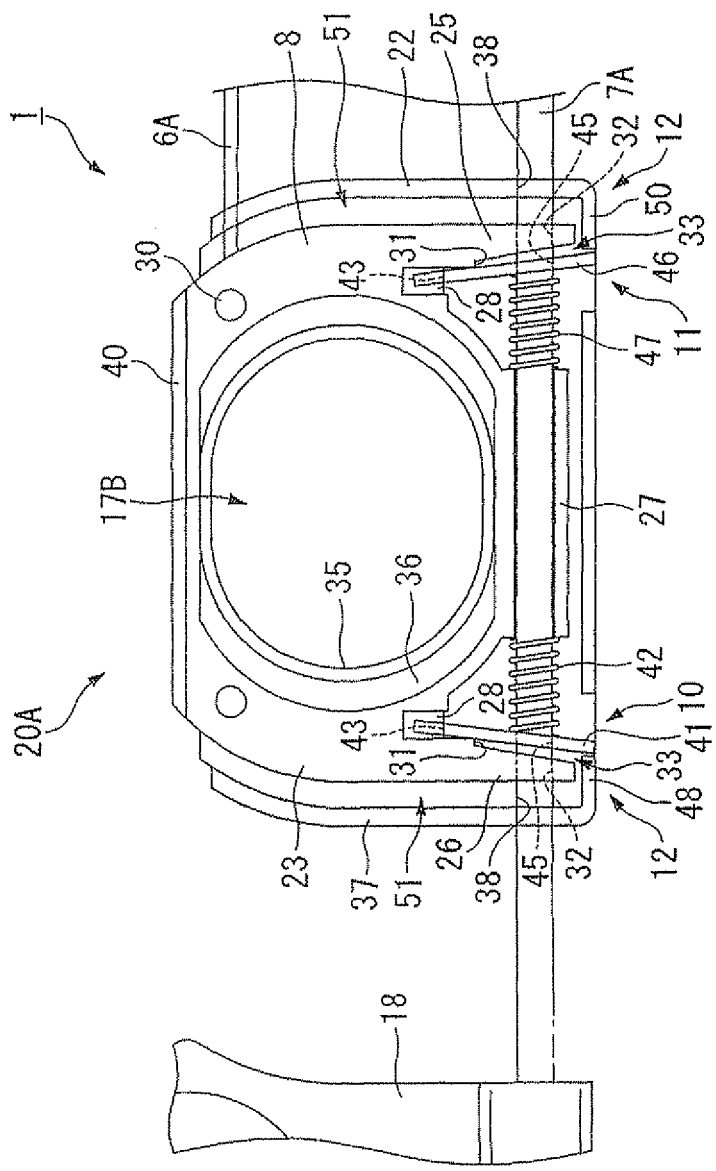
FIG. 4 is a plan view showing the principal part of a static state of the grasping forceps according to the first embodiment of the present invention.
Figure 5:
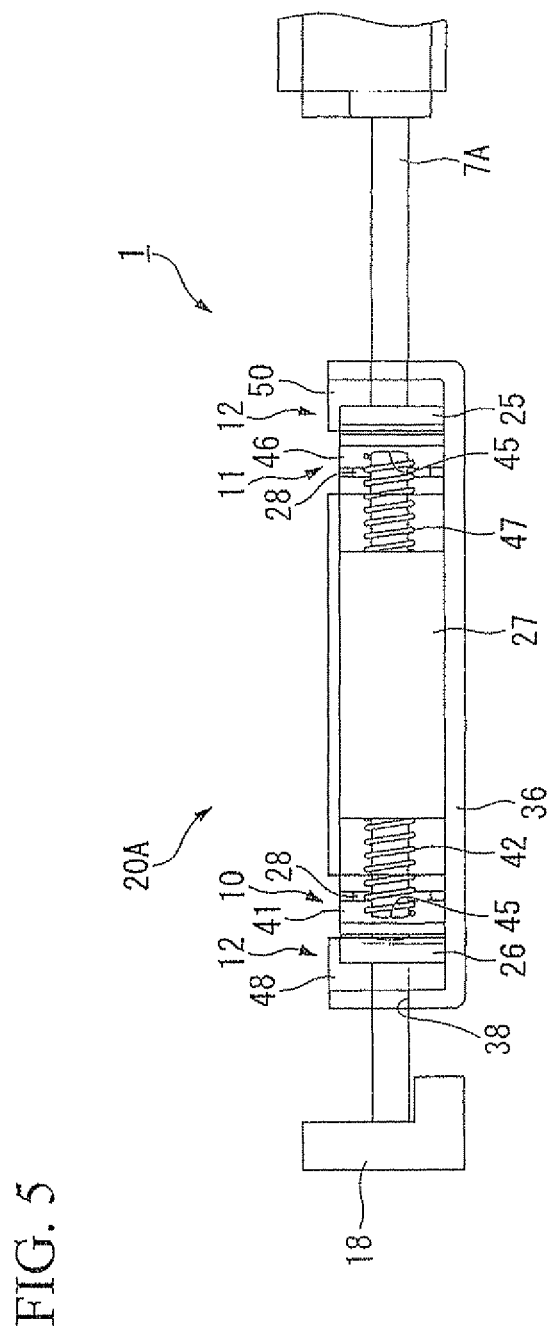
FIG. 5 is a side view of FIG. 4.

As illustrated in FIGS. 4 and 5, the rear locking plate 41 pushed by the first urging section 42 makes contact with the cornered section 31 of the proximal end projection section 26 in the vicinity of the U-letter-shaped groove 43. This state of rear locking plate 41 is fixed and inclines slightly with respect to the axial line direction of the guide section 7A by a backlash provided between the hole section 45 and the guide section 7A. Therefore, the maneuvering wire 6A, i.e., when the extending-and-retracting member 8 attempts to move toward the distal end (right-hand in FIG. 4) relative to the guide section 7A, the rear locking plate 41 pushed by the proximal end projection section 26 attempts to move, since the rear locking plate 41 further inclines relative to the guide section 7A like a wedge in a fixed state to the guide section 7A, movement is prevented.

On the other hand, the U-letter-shaped groove 43 of the front-locking plate 46 pushed by the second urging section 47 makes contact with the cornered section 31 of the distal end projection section 25. This state of front-locking plate 46 is fixed and inclines slightly with respect to the axial line direction of the guide section 7A by a backlash provided between the hole section 45 and the guide section 7A. Therefore, the maneuvering wire 6A, i.e., when the extending-and-retracting member 8 attempts to move toward the proximal end (left-hand in FIG. 4) relative to the guide section 7A, the front locking plate 76 pushed by the distal end projection section 25 attempts to move, since the front locking plate 46 further inclines relative to the guide section 7A like a wedge in a fixed state to the guide section 7A, movement is prevented similarly to the case of rear locking plate 41.

This results in that movement of the maneuvering wire 6A is limited in both toward the proximal end and toward the distal end; therefore, the pair of grasping jaws 13A and 13B do not open or close.

Activities of opening and closing this state of the pair of grasping jaws 13A and 13B will be explained.

To start with, in order to move the maneuvering wire 6A toward the distal end (right-hand in FIGS. 7 and 8), finger hook sections 17A and 17B of the slider section 20A and the fixed handle 18 each accept a finger, and then the slider section 20A is moved toward the distal end.

This state of the rear-locking-plate holder section 48 of the releasing member 22 makes contact with the end section of the rear locking plate 41 since this state of the releasing member 22 can freely move relative to the extending-and-retracting member 8 in a predetermined backlash. Subsequently, the second space 51 causes the releasing member 22 to further move toward the distal end relative to the extending-and-retracting member 8 and causes the end section of the hole section 45 of the rear locking plate 41 to be pressed toward the distal end relative to the end section of the U-letter-shaped groove 43. This state of the rear locking plate 41 presses and compresses the first urging section 42 while displacing in the direction orthogonal to the axial line direction of the guide section 7A to obtain the same inclination direction as that of the front-locking plate 46. This alleviates wedge state, which will resolve in due course, between the hole section 45 and the guide section 7A.

On the other hand, displacement of the front-locking plate 46 relative to the extending-and-retracting member 8 does not change since the front-locking plate 46 pushed by the lateral surface of the distal end projection section 25 of the extending-and-retracting member 8 moves with the extending-and-retracting member 8. Therefore, the front-locking plate 46 moves while maintaining the current inclination relative to the guide section 7A.

Displacement input from the extending-and-retracting member 8 to the maneuvering wires 6A and 6B activates the pair of grasping jaws 13A and 13B.

Figure 9:
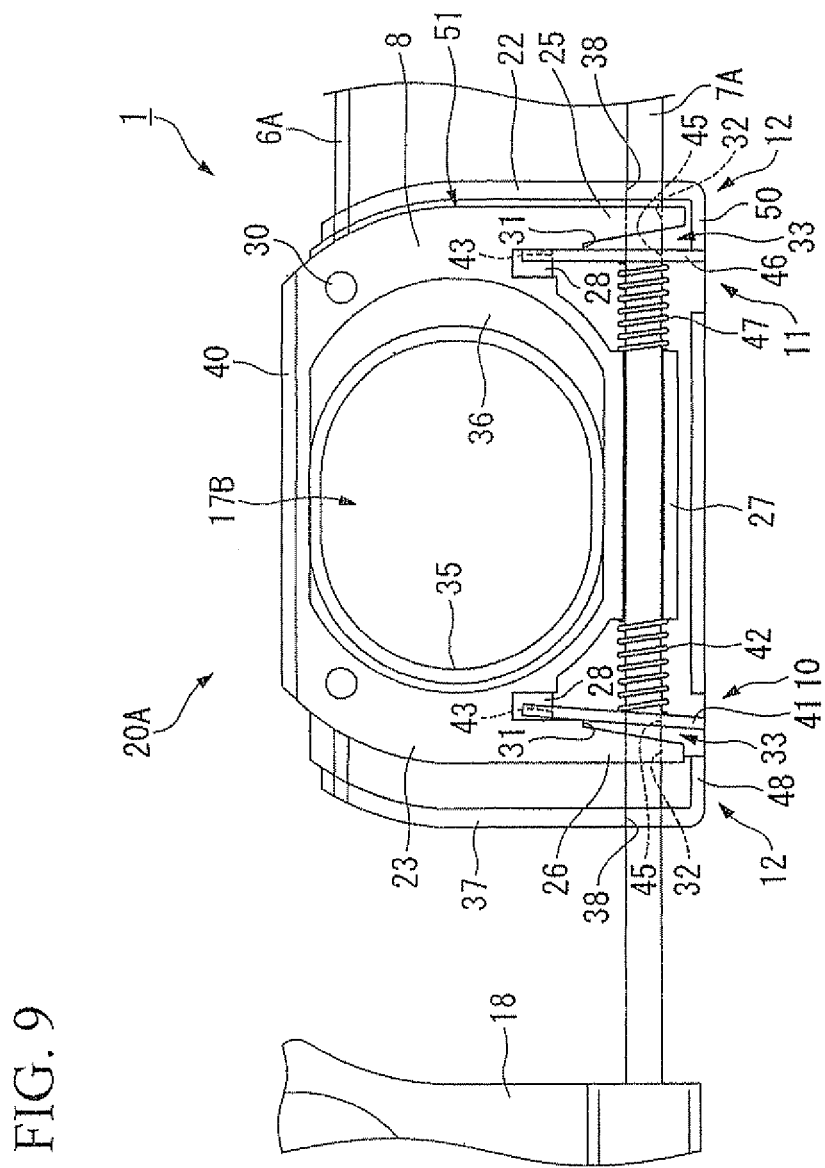
FIG. 9 shows how to close the grasping forceps according to the first embodiment of the present invention.
Figure 10:
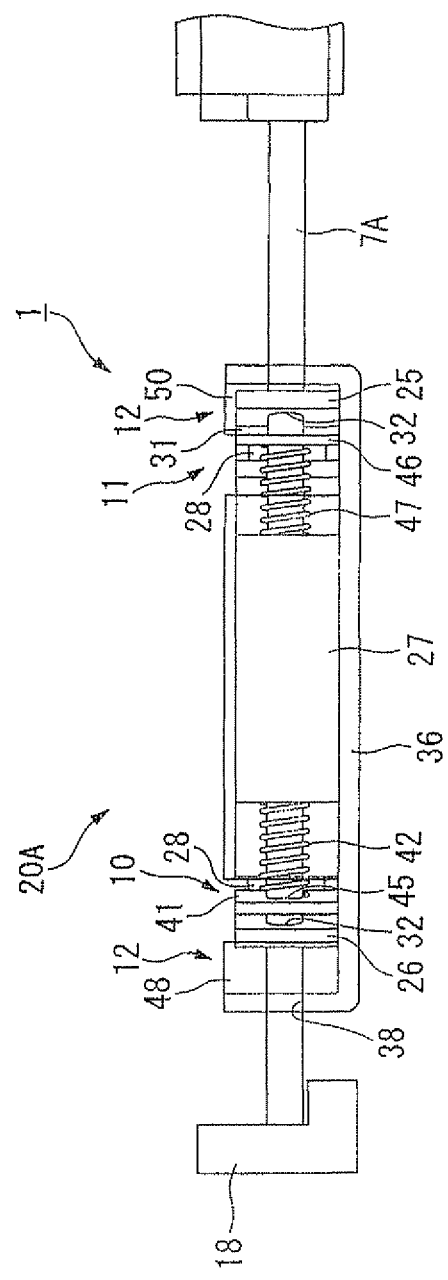
FIG. 10 is a side view of FIG. 9.

Subsequently, the maneuvering wire 6A is moved toward the proximal end (left-hand in FIGS. 9 and 10). Fingers are inserted into this state of the finger hook sections 17A and 17B formed to the slider section 20A and the fixed handle 18, and then the slider section 20A is moved toward the proximal end.

This state of the front-locking-plate holder section 50 of the releasing member 22 makes contact with the end section of the front-locking plate 46 since the releasing member 22 freely moves relative to the extending-and-retracting member 8 in the predetermined backlash. Subsequently, the second space 51 formed between the extending-and-retracting member 8 and the releasing member 22 causes the releasing member 22 to further move toward the proximal end relative to the extending-and-retracting member 8 and causes the end section of the hole section 45 of the front-locking plate 46 to be pressed toward the proximal end relative to the end section of the U-letter-shaped groove 43. This state of the front-locking plate 46 presses and compresses the second urging section 47 while displacing in the direction orthogonal to the axial line direction of the guide section 7A to obtain the same inclination direction as that of the rear-locking plate 41. This alleviates wedge state, which will resolve in due course, between the hole section 45 and the guide section 7A.

On the other hand, displacement of the rear locking plate 41 relative to the extending-and-retracting member 8 does not change since the rear locking plate 41 pushed by the lateral surface of the proximal end projection section 26 of the extending-and-retracting member 8 moves with the extending-and-retracting member 8. Therefore, the front-locking plate 46 moves while maintaining the current inclination relative to the guide section 7A.

Displacement in the direction opposite to the aforementioned case input thereinto activates the pair of grasping jaws 13A and 13B in the opposite direction.

The grasping forceps 1 can maintain the attitude of the intervention section 3 by moving the maneuvering wires 6A and 6B only toward the proximal end of the sheath 2 by means of the distal direction movement inhibitor section 10 even if an external force directed toward the distal end of the sheath 2 is applied to the maneuvering wires 6A and 6B when a certain attitude of the intervention section 3 must be maintained that is activated based on displacement input from the maneuvering section 5.

In addition, the proximal direction movement inhibitor section 11 irrespective of an external force directed toward the proximal end of the sheath 2 can move the maneuvering wires 6A and 6B only toward the distal end of the sheath 2; therefore, a certain attitude of the intervention section 3 can be maintained.

Therefore, the desirable attitude of the intervention section 3 can be maintained during an intervention unless the intervention section 3 is manipulated intentionally by the maneuvering section 5. Also, manipulating of the intervention section 3 and releasing of a certain attitude of the intervention section 3 are identical operations that can be carried out simultaneously.

In particular, inclination (wedge state) between the rear locking plate 41 and the guide section 7A can be maintained, and the fixed state of the maneuvering wires 6A and 6B to the guide section 7A can also be maintained irrespective to an attempt of moving the maneuvering wires 6A and 6B toward the distal end by means of an external force since the rear locking plate 41 is urged by the first urging section 42.

On the other hand, inclination (wedge state) between the front-locking plate 46 and the guide section 7A can be maintained, and the fixed state of the maneuvering wire 6A to the guide section 7A can be maintained since the front-locking plate 46 is urged by the second urging section 47 irrespective to an attempt of moving the maneuvering wire 6A toward the proximal end. Therefore, a desirable attitude of the intervention section 3 can be maintained even if an external force is applied in any directions.

In addition, moving the releasing member 22 relative to the extending-and-retracting member 8 in one of directions toward the distal end or the proximal end of the sheath 2 may change inclination of the guide section 7A relative to the rear locking plate 41 or the front-locking plate 46, thereby resolve the wedge state between the hole section 45 and the guide section 7A. Therefore, the maneuvering wires 6A and 6B can be moved in moving directions of the slider sections 20A and 20B by releasing limitation with respect to movement of the maneuvering wires 6A and 6B.

A second embodiment of the present invention will be explained next with reference to FIGS. 11 to 13.

Here, the same reference numeral are added to elements as those shown in the first embodiment; thus, explanations therefore are omitted.

The second embodiment relating to a grasping forceps 60 having a specific directional movement-inhibitor section 61 disposed on the distal end of the sheath 2 is different from the first embodiment relating to the grasping forceps 1 having the distal direction movement inhibitor section 10 and the proximal direction movement inhibitor section 11 disposed on the maneuvering section 5.

In addition, the grasping forceps 60 is provided with: the sheath 2; an intervention section 62 disposed on the distal end 2a of the sheath 2; a maneuvering section 63 disposed on the proximal end 2b of the sheath 2; a maneuvering wire 65 freely extending and retracting relative to the sheath 2 in the direction of the axial line C; an extending-and-retracting member 66, disposed on the axial line C, having a shaft shape and having the intervention section 62 on the distal end; a cylindrical guide section 67 connected to the distal end 2a of the sheath 2 and to the proximal end of a frame 73 which will be explained later; and a locked-state-releasing section 68 disposed in the guide section 67 and connected to the distal end of the maneuvering wire 65.

The intervention section 62 is provided with: a pair of grasping jaws 70A and 70B; links 71A and 71B, respectively connected to the pair of grasping jaws 70A and 70B, that convert the displacement input thereinto based on the extending and retracting control associated with the maneuvering wire 65 into output associated with opening and closing of the pair of grasping jaws 70A and 70B; and a frame 73 rotatively fixing ends of the pair of grasping jaws 70A and 70B and ends of the links 71A and 71B by means of rotative shafts 72.

The maneuvering section 63 is provided with a maneuvering section main unit 63A having the proximal end of the sheath 2 connected thereto; and a slider section 63B, disposed to freely extend and retract relative to the maneuvering section main unit 63A, and having the proximal end of the maneuvering wire 65 thereto.

The extending-and-retracting member 66 is provided with: an increased-diameter section 66A disposed on the distal end; a reduced diameter section 66B disposed in the vicinity of the proximal end relative to the increased-diameter section 66A and having a diameter smaller than that of the increased-diameter section 66A; a first taper section 66C, disposed between the increased-diameter section 66A and the reduced diameter section 66B, and gradually reducing an outer diameter thereof from the increased-diameter section 66A to the reduced diameter section 66B; and a second taper section 66D having an outer diameter that gradually increases from the reduced diameter section 66B to the proximal end of the extending-and-retracting member 66. A distal end flange section 66E having a greater outer diameter than that of the increased-diameter section is connected to a border section between the increased-diameter section 66A and the first taper section 66C. Provided to the proximal end of the extending-and-retracting member 66 is a proximal end flange section 66F having the same diameter as that of the distal end flange section 66E. The other ends of the links 71A and 71B are connected rotatively to the distal end of the increased-diameter section 66A via the links 71A and 71B.

A cylindrically formed locked-state-releasing section 68 has an outer diameter and an inner diameter that allow the locked-state-releasing section 68 to slide in the guide section 67 and allow a section of the extending-and-retracting member 66 from the distal end flange section 66E to the proximal end to slide in the locked-state-releasing section 68. A distal end bottom section 68A is disposed on the distal end of the locked-state-releasing section 68. A proximal end bottom section 68B is disposed on the proximal end of the locked-state-releasing section 68. Three slits 76, disposed at an interval of 120 degrees, extending in the direction of the axial line C are formed on the lateral surface of the locked-state-releasing section 68.

The slits 76 each have size, i.e., widths that hold a distal end bal 77 and a proximal end ball 78, which will be explained later, in order to prevent the balls from moving in a circumferential direction of the extending-and-retracting member 66; and allow the balls to move in an axial line direction of the extending-and-retracting member.

The length (L indicated in the drawings) of the slit 76 based on non-actuated state of the pair of the grasping jaws 70A and 70B is longer than the distance between the distal end ball 77 and the proximal end ball 78 urged by an urging section, which will be explained later. On the other hand, the slits 76 of the locked-state-releasing section 68 are located so that a distance between the end 76a of the slit 76 and the distal end bottom section 68A is the same as a distance between the other end 76b of the slit 76 and the proximal end bottom section 68B. Reference symbol "A" indicates the distance. The distance A is adjusted to be greater than a difference between the length of each slit 76 and the distance IL indicated by reference symbol "B," in the drawings.

The both ends 76a and 76b of each slit 76 serve as fixed-state-releasing sections having the function of moving the distal end ball 77 or the proximal end ball 78 relative to the guide section 67.

Provided to the distal end bottom section 68A is a through-hole 68a that allows the increased-diameter section 66A of the extending-and-retracting member 66 to pass therethrough. In addition, the maneuvering wire 65 is fixed and crimped onto the proximal end bottom section 68B.

The specific directional movement-inhibitor section 61 is provided with: the distal end ball (fixing section) 77, guided by the slit 76 of the locked-state-releasing section 68, that moves in the axial line direction of the extending-and-retracting member 66 freely between the surface above the first taper section 66C of the extending-and-retracting member 66 and the inner surface of the guide section 67; the proximal end ball (fixing section) 78, guided by the slit 76 of the locked-state-releasing section 68, that moves in the axial line direction of the extending-and-retracting member 66 freely between the surface above the second taper section 66D of the extending-and-retracting member 66 and the inner surface of the guide section 67; and the urging section 80, i.e., a spring that is disposed between the distal end ball 77 and the proximal end ball 78 to urge the balls in the separating direction.

The distal end ball 77 and the proximal end ball 78 have predetermined outer diameters, that are smaller than the distance between the outer periphery of the reduced diameter section 66B of the extending-and-retracting member 66 and the inner periphery of the guide section 67 and greater than the distance between the outer periphery of the increased-diameter section 66A and the inner periphery of the guide section.

Each slit 76 has three distal end balls 77 and three proximal end balls 78.

The urging section 80 has an urging force that presses the distal end ball 77 onto the first taper section 66C and presses the proximal end ball 78 onto the second taper section 66D.

The operation and effect of the grasping forceps 60 according to the present embodiment will be explained next.

Activities will be explained first with respect to maintaining a static state of the pair of grasping jaws 70A and 703B upon undergoing an external force applied thereto and attempting to open and close the pair of grasping jaws 70A and 701B while the maneuvering section 63 is not manipulated.

An external force applied to move the extending-and-retracting member 66 along the axial line direction shown in FIG. 11 toward the distal end (left-hand in FIG. 11) causes the proximal end ball 78 to further engage with the second taper section 66D and the guide section 67, thereby preventing movement of the extending-and-retracting member 66 fixed to the guide section 67.

Similarly, an external force applied to move the extending-and-retracting member 66 along the axial line direction shown in FIG. 11 toward the proximal end (right-hand in FIG. 11) causes the distal end ball 77 to further engage with the first taper section 66C and the guide section 67, thereby preventing movement of the extending-and-retracting member 66 fixed to the guide section 67.

This results in that movement of the extending-and-retracting member 66 is limited in both toward the proximal end and toward the distal end; therefore, the pair of grasping jaws 70A and 70B do not open or close.

Activities for opening and closing this state of the pair of grasping jaws 70A and 70B will be explained.

Figure 12:
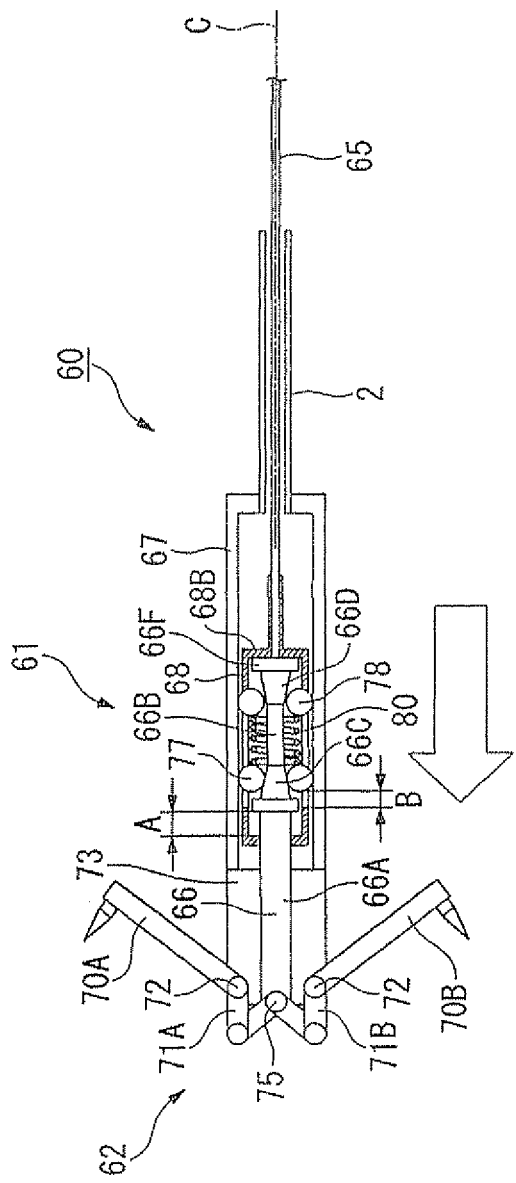
FIG. 12 is a schematic view showing how to open the grasping forceps according to the second embodiment of the present invention.

As illustrated in FIG. 12, opening of the pair of grasping jaws 70A and 70B necessitates moving the slider section 63B toward the distal end in order to move the maneuvering wire 65 toward the distal end (left-hand in FIG. 12).

The locked-state-releasing section 68 alone moves toward the distal end relative to the guide section 67 based on the movement of this state of maneuvering wire 65 toward the distal end. That is, the slits 76 move relative to the distal end balls 77 and the proximal end balls 78. Subsequently, the other ends 76b of the slits 76 make contact with the proximal end balls 78. Moving the maneuvering wire 65 furthermore causes the other ends 76b of the slits 76 to press and move the urging section 80 toward the distal end while moving the proximal end balls 78 toward the distal end.

This state of the distal end balls 77 move in the direction that engages with the surface of the first taper section 66C and the inner surface of the guide section 67. However, moving further the maneuvering wire 65 causes the proximal end bottom section 68B of the locked-state-releasing section 68 to make contact with and compress the proximal end flange section 66F of the extending-and-retracting member 66. This results in moving the extending-and-retracting member 66 relative to the distal end balls 77 and alleviating the wedge state of the distal end ball 77 relative to the first taper section 66C and the guide section 67, thereby releasing the fixed state of the distal end ball 77 relative to the first taper section 66C and the inner surface of the guide section 67.

This results in that the distal end balls 77 and the proximal end balls 78 are free relative to the guide section 67, thereby moving both the extending-and-retracting member 66 and the locked-state-releasing section 68.

Accordingly, the displacement of the maneuvering wire 65 input and transmitted to the extending-and-retracting member 66 is converted by the links 71A and 71B into a force that opens the pair of grasping jaws 70A and 70B.

Figure 13:
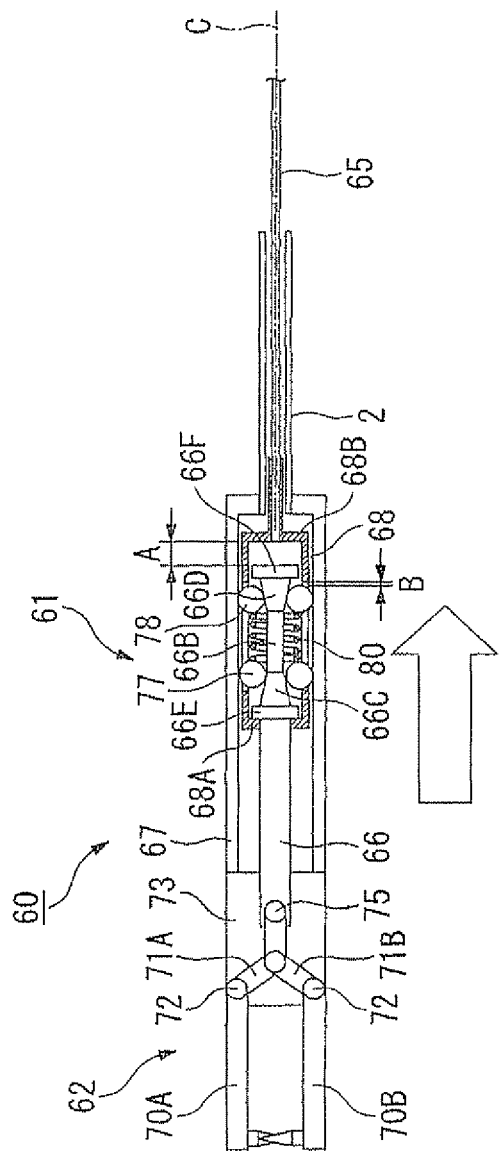
FIG. 13 is a schematic view showing how to close the grasping forceps according to the second embodiment of the present invention.

As illustrated in FIG. 13, closing of the pair of grasping jaws 70A and 70B necessitates moving the maneuvering wire 65 toward the proximal end in order to move the slider section 63B3 toward the proximal end (right-hand in FIG. 13).

The locked-state-releasing section 68 alone moves toward the proximal end relative to the guide section 67 based on the movement of this state of maneuvering wire 65. The movement of the slits 76 relative to the distal end balls 77 causes the ends 76a of the slits 76 to make contact with the distal end balls 77. Accordingly, movement of the distal end balls 77 toward the proximal end presses and moves the urging section 80.

This state of the proximal end balls 78 move in the direction that engages with the surface of the second taper section 66D and the inner surface of the guide section 67. However, moving further the maneuvering wire 65 causes the distal end bottom section 68A of the locked-state-releasing section 68 to make contact with and compress the distal end flange section 66E of the extending-and-retracting member 66. This results in moving the extending-and-retracting member 66 relative to the proximal end balls 78 and alleviating the wedge state of the proximal end balls 78 relative to the second taper section 66D and the guide section 67, thereby releasing the fixed state of the proximal end balls 78 relative to the second taper section 66D and the inner surface of the guide section 67.

This results in that the distal end balls 77 and the proximal end balls 78 are free relative to the guide section 67, thereby moving both the extending-and-retracting member 66 and the locked-state-releasing section 68.

Accordingly, the displacement of the maneuvering wire 65 input and transmitted to the extending-and-retracting member 66 is converted by the links 71A and 71B into a force that closes the pair of grasping jaws 70A and 70B.

The grasping forceps 60 can prevent movement of the extending-and-retracting member 66 in the vicinity of the intervention section 62 more effectively than, e.g., the first embodiment that prevents movement of the extending-and-retracting member 66 caused by an external force in the vicinity of the proximal end of the sheath 2, i.e., in the maneuvering section 63. Therefore, opening and closing of the pair of non-actuated grasping jaws 70A and 70B caused by an external force can be prevented more reliably.

The technical scope of the present invention is not limited to the embodiments described above. Rather, various modifications may be added provided that they do not depart from the spirit of the invention.

For example, an angular shaft that can engage with the rear locking plate and the hole section of the front locking plate may be used in place of the round shaft guide sections 7A and 7B used in the aforementioned first embodiment. Also, the shaft-shaped guide section may be replaced by another shape of guide section that can move the extending-and-retracting member and the releasing member in the extending direction of the maneuvering wire. Furthermore, a configuration including the two slider sections 20A and 20B and the pair of maneuvering wires 6A and 6B connected to the slider sections 20A and 20B respectively may be replaced by a configuration of the second embodiment including a slider section and a maneuvering wire connected thereto.

Also, the helical spring serving as the urging section may be replaced by another form of elastically deformable spring or a magnetized component, e.g., a magnet.

Furthermore, the medical intervention instrument is not limited to a grasping forceps. A component that provides intervention by extending and retracting a sheath may be used, e.g., a biopsy forceps, a needle knife, an injection needle catheter, or a papillotome.

The present invention can maintain a certain static state of the intervention instrument undergoing an external force applied thereto unless the maneuvering section is manipulated intentionally. Also, manipulating of the intervention instrument and releasing of a certain attitude of the intervention instrument are identical operations that can be carried out simultaneously.

What is claimed is:

1. A medical intervention instrument comprising:
    a sheath having a distal end and a proximal end and extending in an axial direction;
    an intervention instrument disposed to the distal end of the sheath;
    a transmission section that makes extending and retracting movements in an axial line direction relative to the sheath;
    a maneuvering section, disposed to the proximal end of the sheath, that accepts displacement information input thereinto associated with the transmission section relative to the sheath;
    a guide section, fixed in the axial line direction relatively against the sheath, that guides the transmission section in the axial line direction of the sheath;
    a distal direction movement inhibitor section that allows the transmission section to move only in a proximal direction from the distal end of the sheath toward the proximal end of the sheath relative to the guide section; and a proximal direction movement inhibitor section that allows the transmission section to move only in a distal direction from the proximal end of the sheath toward the distal end of the sheath relative to the guide section, wherein the distal direction movement inhibitor section and the proximal direction movement inhibitor section are disposed in the transmission section, the distal direction movement inhibitor section is provided with:
  a first fixing section that is displaced relative to the guide section and engages the guide section with the transmission section or detaches the guide section from the transmission section; and
  a first urging section that urges the first fixing section in a direction that fixes the guide section to the transmission section relatively, and the proximal direction movement inhibitor section is provided with:
  a second fixing section that is displaced relative to the guide section in a direction opposite the first fixing section and engages the guide section with the transmission section or detaches the guide section from the transmission section; and
  a second urging section that urges the second fixing section in a direction that fixes the guide section to the transmission section relatively; and a pair of maneuvering wires configured to move in the sheath in extending and retracting directions along the axial direction of the sheath, wherein:

the transmission section comprises a pair of transmission sections;
the guide section comprises a pair of guide sections;
the distal direction movement inhibitor section comprises a pair of distal direction movement inhibitor sections;
the proximal direction movement inhibitor section comprises a pair of proximal direction movement inhibitor sections;
the first fixing section comprises a rear-locking plate;
the second fixing section comprises a front-locking plate;
the maneuvering section accepts displacement information input thereinto associated with movements of the pair of maneuvering wires relative to the sheath; and
the maneuvering section includes:
  a distal section fixed to the proximal end of the sheath;
  the pair of transmission sections, each of which is fixed and connected to a proximal end of corresponding one of the pair of maneuvering wires and is configured to perform extending and retracting movements in the axial line direction relative to the sheath, each of the pair of transmission sections including:
    a hoop section forming a finger hook section,
    a distal end projection section and a proximal end projection section, both of which extend in parallel in directions of tangential lines of the hoop section,
    a pair of saddle sections, one of which is formed at a section where the hoop section is connected to the distal end projection section and the other of which is formed at a section where the hoop section is connected to the proximal end projection section, and
    a passage section;
  the pair of guide sections fixed to the distal section in the axial line direction relatively against the sheath, each of the pair of guide sections being configured to guide corresponding one of the pair of transmission sections in the axial line direction at the passage section of the one corresponding of the pair of transmission sections;
  the pair of distal direction movement inhibitor sections, each of which is configured to allow corresponding one of the pair of maneuvering wires to move only toward the proximal end of the sheath relative to corresponding one of the pair of guide sections, each of the pair of distal direction movement inhibitor sections including:
    the rear-locking plate configured to be displaced relative to the corresponding one of the pair of guide sections and configured to engage the corresponding one of the pair of guide sections with corresponding one of the pair of transmission sections or detach the corresponding one of the pair of guide sections from the corresponding one of the pair of transmission sections, the rear-locking plate having two ends, one of which has a first groove engaging with the saddle section of the proximal end projection section and the other of which has a first hole section which the corresponding one of the pair of guide sections is inserted in and engaged with, the rear-locking plate being inclinable with respect to a direction orthogonal to the corresponding one of the pair of guide sections in order to be fixed to the corresponding one of the pair of guide sections, and
    the first urging section disposed between the rear-locking plate and the passage section of the corresponding one of the pair of transmission sections and configured to urge the rear-locking plate in a direction that fixes the corresponding one of the pair of guide sections to the corresponding one of the pair of transmission sections relatively;
  the pair of proximal direction movement inhibitor sections, each of which is configured to allow corresponding one of the pair of maneuvering wires to move only toward the distal end of the sheath relative to corresponding one of the pair of guide sections, each of the pair of proximal direction movement inhibitor sections including:
    the front-locking plate configured to be displaced relative to the corresponding one of the pair of guide sections in a direction opposite the corresponding rear-locking plate and configured to engage the corresponding one of the pair of guide sections with corresponding one of the pair of transmission sections or detach the corresponding one of the pair of guide sections from the corresponding one of the pair of transmission sections, the front-locking plate having two ends, one of which has a second groove engaging with the saddle section of the distal end projection section and the other of which has a second hole section which the corresponding one of the pair of guide sections is inserted in and engaged with, the front-locking plate being inclinable with respect to a direction orthogonal to the corresponding one of the pair of guide sections in order to be fixed to the corresponding one of the pair of guide sections, the front-locking plate and the corresponding rear-locking plate being inclinable in opposite directions, and
    the second urging section disposed between the front-locking plate and the passage section of the corresponding one of the pair of transmission sections and configured to urge the front-locking plate in a direction that fixes the corresponding one of the pair of guide sections to the corresponding one of the pair of transmission sections relatively; and a pair of locked-state releasing sections, each of which includes:
  a rear-locking-plate holder section configured to press and displace the corresponding rear-locking plate in a direction of releasing a fixed state between the corresponding rear-locking plate and corresponding one of the pair of guide sections, and
  a front-locking-plate holder section configured to press and displace the corresponding front-locking plate in a direction of releasing a fixed state between the corresponding front-locking plate and the corresponding one of the pair of guide sections.

2. The medical intervention instrument according to claim 1, further comprising a locked-state releasing section capable of alternatively releasing engagement of the guide section with the distal direction movement inhibitor section and engagement of the guide section with the proximal direction movement inhibitor section.

3. The medical intervention instrument according to claim 1, further comprising a locked-state releasing section capable of choosing from a state in which engagement of the guide section with the distal direction movement inhibitor section is released, a state in which engagement of the guide section with the proximal direction movement inhibitor section is released, and a state in which the guide section engages with each of the distal direction movement inhibitor section and the proximal direction movement inhibitor section.

4. The medical intervention instrument according to claim 1, further comprising a locked-state releasing section configured to release engagement of the guide section with the distal direction movement inhibitor section by moving the locked-state releasing section in the distal direction so that the transmission section is allowed to move in the distal direction, and release engagement of the guide section with the proximal direction movement inhibitor section by moving the locked-state releasing section in the proximal direction so that the transmission section is allowed to move in the proximal direction.

5. A medical intervention instrument comprising:
a sheath having a distal end and a proximal end and extending in an axial direction;
an intervention section disposed to the distal end of the sheath;
a transmission section that makes extending and retracting movements in an axial line direction relative to the sheath;
a maneuvering section, disposed to the proximal end of the sheath, that accepts displacement information input thereinto associated with the transmission section relative to the sheath;
a guide section, fixed in the axial line direction relatively against the sheath, that guides the transmission section in the axial line direction of the sheath;
a specific directional movement-inhibitor section that allows the transmission section to move only in one of a distal direction from the proximal end of the sheath toward the distal end of the sheath and a proximal direction from the distal end of the sheath toward the proximal end of the sheath relative to the guide section; and a locked-state-releasing section that releases an engaging state between the guide section and the specific directional movement-inhibitor section based on a displacement in another of the distal direction and the proximal direction, the displacement being input by the maneuvering section, wherein the specific directional movement-inhibitor section is disposed in the transmission section, the specific directional movement-inhibitor section is provided with:
  a distal direction movement inhibitor section that allows the transmission section to move only in the proximal direction relative to the guide section;
  a proximal direction movement inhibitor section that allows the transmission section to move only in the distal direction relative to the guide section;
  a fixing section that is displaced relative to the guide section and engages the guide section with the transmission section or detaches the guide section from the transmission section; and
  an urging section that displaces the fixing section in a direction that fixes the guide section to the transmission section relatively, and the locked-state-releasing section is provided with a fixed-state-releasing section that displaces the fixing section against the urging force of the urging section in a direction that releases the fixed state between the fixing section and the guide section; and a pair of maneuvering wires configured to move in the sheath in extending and retracting directions along the axial direction of the sheath, wherein:

the transmission section comprises a pair of transmission sections;

the guide section comprises a pair of guide sections;

the distal direction movement inhibitor section comprises a pair of distal direction movement inhibitor sections;

the proximal direction movement inhibitor section comprises a pair of proximal direction movement inhibitor sections;

the fixing section comprises a rear-locking plate and a front-locking plate;

the urging section comprises a first urging section and a second urging section;

the locked-state releasing section comprises a pair of locked-state releasing sections;

the maneuvering section accepts displacement information input thereinto associated with movements of the pair of maneuvering wires relative to the sheath; and the maneuvering section includes:
  a distal section fixed to the proximal end of the sheath;
  the pair of transmission sections, each of which is fixed and connected to a proximal end of corresponding one of the pair of maneuvering wires and is configured to perform extending and retracting movements in the axial line direction relative to the sheath, each of the pair of transmission sections including:
    a hoop section forming a finger hook section,
    a distal end projection section and a proximal end projection section, both of which extend in parallel in directions of tangential lines of the hoop section,
    a pair of saddle sections, one of which is formed at a section where the hoop section is connected to the distal end projection section and the other of which is formed at a section where the hoop section is connected to the proximal end projection section, and a passage section;

the pair of guide sections fixed to the distal section in the axial line direction relatively against the sheath, each of the pair of guide sections being configured to guide corresponding one of the pair of transmission sections in the axial line direction at the passage section of the corresponding one of the pair of transmission sections;

the pair of distal direction movement inhibitor sections, each of which is configured to allow corresponding one of the pair of maneuvering wires to move only toward the proximal end of the sheath relative to corresponding one of the pair of guide sections, each of the distal direction movement inhibitor section including:

the rear-locking plate configured to be displaced relative to the corresponding one of the pair of guide sections and configured to engage the corresponding one of the pair of guide sections with corresponding one of the pair of transmission sections or detach the corresponding one of the pair of guide sections from the corresponding one of the pair of transmission sections, the rear-locking plate having two ends, one of which has a first groove engaging with the saddle section of the proximal end projection section and the other of which has a first hole section which the corresponding one of the pair of guide sections is inserted in and engaged with, the rear-locking plate being inclinable with respect to a direction orthogonal to the corresponding one of the pair of guide sections in order to be fixed to the corresponding one of the pair of guide sections, and the first urging section disposed between the rear-locking plate and the passage section of the corresponding one of the pair of transmission sections and configured to urge the rear-locking plate in a direction that fixes the corresponding one of the pair of guide sections to the corresponding one of the pair of transmission sections relatively;

the pair of proximal direction movement inhibitor sections, each of which is configured to allow corresponding one of the pair of maneuvering wires to move only toward the distal end of the sheath relative to corresponding one of the pair of guide sections, each of the pair of proximal direction movement inhibitor sections including:

the front-locking plate configured to be displaced relative to the corresponding one of the pair of guide sections in a direction opposite the corresponding rear-locking plate and configured to engage the corresponding one of the pair of guide sections with corresponding one of the pair of transmission sections or detach the corresponding one of the pair of guide sections from the corresponding one of the pair of transmission sections, the front-locking plate having two ends, one of which has a second groove engaging with the saddle section of the distal end projection section and the other of which has a second hole section which the corresponding one of the pair of guide sections is inserted in and engaged with, the front-locking plate being inclinable with respect to a direction orthogonal to the corresponding one of the pair of guide sections in order to be fixed to the corresponding one of the pair of guide sections, the front-locking plate and the corresponding rear-locking plate being inclinable in opposite directions, and the second urging section disposed between the front-locking plate and the passage section of the corresponding one of the pair of transmission sections and configured to urge the front-locking plate in a direction that fixes the corresponding one of the pair of guide sections to the corresponding one of the pair of transmission sections relatively; and the pair of locked-state releasing section, each of which includes:

a rear-locking-plate holder section configured to press and displace the corresponding rear-locking plate in a direction of releasing a fixed state between the corresponding rear-locking plate and corresponding one of the pair of guide sections, and a front-locking-plate holder section configured to press and displace the corresponding front-locking plate in a direction of releasing a fixed state between the corresponding front-locking plate and the corresponding one of the pair of guide sections.

6. The medical intervention instrument according to claim 5, wherein the locked-state-releasing section is capable of alternatively releasing engagement of the guide section with the distal direction movement inhibitor section and engagement of the guide section with the proximal direction movement inhibitor section.

7. The medical intervention instrument according to claim 5, wherein the locked-state releasing section is capable of choosing from a state in which engagement of the guide section with the distal direction movement inhibitor section is released, a state in which engagement of the guide section with the proximal direction movement inhibitor section is released, and a state in which the guide section engages with each of the distal direction movement inhibitor section and the proximal direction movement inhibitor section.

8. The medical intervention instrument according to claim 5, wherein the locked-state releasing section is configured to release engagement of the guide section with the distal direction movement inhibitor section by moving the locked-state releasing section in the distal direction so that the transmission section is allowed to move in the distal direction, and release engagement of the guide section with the proximal direction movement inhibitor section by moving the locked-state releasing section in the proximal direction so that the transmission section is allowed to move in the proximal direction.

* * * * *